United States Patent
Hess et al.

(10) Patent No.: US 6,180,664 B1
(45) Date of Patent: Jan. 30, 2001

(54) PENTAERYTHRITOL DERIVATIVES, THEIR PRODUCTION AND USE AND INTERMEDIATES FOR THEIR SYNTHESIS

(75) Inventors: Ulrich Hess; Anne-Katrin Windeck; Holger Brosig, all of Berlin (DE)

(73) Assignee: ISIS Pharma GmbH, Monheim (DE)

(*) Notice: Under 35 U.S.C. 154(b), the term of this patent shall be extended for 0 days.

(21) Appl. No.: 09/269,969

(22) PCT Filed: Oct. 10, 1997

(86) PCT No.: PCT/DE97/02328

§ 371 Date: Jun. 8, 1999

§ 102(e) Date: Jun. 8, 1999

(87) PCT Pub. No.: WO98/15521

PCT Pub. Date: Apr. 16, 1998

(30) Foreign Application Priority Data

| Oct. 10, 1996 | (DE) | 196 41 667 |
| Dec. 17, 1996 | (DE) | 196 52 345 |
| Jun. 25, 1997 | (DE) | 197 26 812 |

(51) Int. Cl.[7] ................. C07C 203/04; A61K 31/21
(52) U.S. Cl. ................. 514/509; 514/506; 558/483; 558/484
(58) Field of Search ................. 558/484, 486; 568/853; 562/564, 565; 560/158; 564/203, 151; 514/506, 509, 574

(56) References Cited

U.S. PATENT DOCUMENTS

| 1,883,045 | 10/1932 | Spaeth . |
| 2,389,228 | 11/1945 | Wyler .................... 260/467 |
| 3,251,739 | 5/1966 | Petersen et al. ............ 167/65 |

FOREIGN PATENT DOCUMENTS

| 6487 | 11/1968 | (FR) . |
| 442850 | 11/1934 | (GB) . |

OTHER PUBLICATIONS

Evans et al., "Some ethers of pentaerythritol and their nitrate esters," *Journal of the American Chemical Society*, vol. 75, 1953, pp. 1248–1249.

Nec, "Oxidation of some pentaerythritol monoacetals," *Chem. Prum.*, 78; vol. 28(2), pp. 84–86, (1977).

Zeman et al., "Trimethylolmethane derivatives, nitrates," *Chemical Abstracts*, vol. 105, No. 23, Dec. 8, 1986.

Faubion, "Study of high explosives by optical thermal analysis," *Anal. Chem.*, vol. 43, pp. 241–247, (1971).

Marans et al., "Organic acid esters of pentaerythritol trinitrate," *Journal of the American Chemical Society*, vol. 76, 1954, pp. 1304–1306.

Marans et al., "Nitrate esters of 2,2–dimethylol–1–propanol monoacetate and diacetate," *Journal of the American Chemical Society*, vol. 76, 1954, pp. 3223–3224.

Tsang et al., The nitration of toluene with alkyl nitrates and polyphosphoric acid, *Journal of Organic Chemistry*, vol. 29, 1964, pp. 3387–3390.

*Primary Examiner*—Deborah C. Lambkin
*Assistant Examiner*—Ebenezer Sackey
(74) *Attorney, Agent, or Firm*—Marshall, O'Toole, Gerstein, Murray & Borun

(57) ABSTRACT

The invention describes novel compounds derived from pentaerythritol of general formula I, XIV, XVI, XIX and XXII, the substituents being as defined in the description, which can be used as pharmaceutical active substances, especially for the treatment of cardiovascular diseases.

(I)

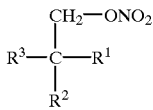

27 Claims, No Drawings

PENTAERYTHRITOL DERIVATIVES, THEIR PRODUCTION AND USE AND INTERMEDIATES FOR THEIR SYNTHESIS

This application is a 371 of PCT/DE 97/02328 filed Oct. 10, 1997.

FIELD OF APPLICATION OF THE INVENTION

The present invention relates to novel pentaerythritol derivatives, to the preparation and use thereof, especially as drugs, and to intermediates for the synthesis thereof.

KNOWN TECHNICAL BACKGROUND

Organic nitric acid esters such as glycerol trinitrate (GTN) (Murrel, Lancet: 80, 113, 151 (1879)), pentaerythrityl tetranitrate (PETN) (Risemann et al., Circulation, Vol. XVII, 22 (1958), U.S. Pat. No. 2,370,437), isosorbide-5-mononitrate (ISMN) (DE-OS-2221080 DE-OS-2751934DE-PS-3028873, DE-OS-2903927, DE-OS-3102947, DE-OS-3124410, EP-A1-045076, EP-A1-057847, EP-A1-059664, EP-A1-064194, EP-A1-067964, EP-A1-143507, U.S. Pat. No. 3,886,186, U.S. Pat. No. 4,065,488, U.S. Pat. No. 4,417,065, U.S. Pat. No. 4,431,829), isosorbide dinitrate (ISDN) (L. Goldberg, Acta Physiolog. Scand. 15, 173 (1948)), propatyl nitrate (Medard, Mem. Poudres 35: 113 (1953)), trolnitrate (FR-PS 984523) or nicorandil (U.S. Pat. No. 4,200,640) and similar compounds are vasodilators, some of which have been used very widely for decades as major drugs in the therapy of the indication angina pectoris or ischaemic heart disease (IHD) (Nitrangin®, Pentalong®, Monolong®, etc.). Other pentaerythrityl nitrates and their preparation have likewise been described (Simecek, Coll. Czech. Chem. Comm. 27 (1962), 363; Camp et al., J. Am. Chem. Soc. 77 (1955), 751). Organic "nitrates" of a more recent type, for example SPM 3672 (N-[3-nitratopivaloyl]-L-cysteine ethyl ester) (U.S. Pat. No. 5,284,872) and derivatives thereof or 1,4-dihydropyridine derivatives (WO-A1-92/02503), have a comparable and improved pharmacological efficacy when used in the above-mentioned areas of indication. In addition to the applications of nitrosating substances which have been known for many years, their use for the treatment and prevention of diseases caused by pathologically increased concentrations of sulfur-containing amino acids in body fluids has been described. These pathological conditions, brought about by congenital or acquired defects in the metabolism of these amino acids and characterized by increased blood and urine concentrations of said amino acids (homocystinuria), are collectively described by the term homocysteinaemia (WO-A1-92/18002). Other uses of the above substances have recently been described, for instance as endothelium-protecting agents (DE-A1-4410997), agents for the treatment of pathologically increased intraocular pressure (WO-A1-95/13812), agents for the treatment of dysmenorrhoea, dysfunctional uterine bleeding, premature labour or after-pains by reducing the uterine contractility (WO-A1-95/13802), agents for the treatment of menopausal symptoms (WO-A1-95/13800) or agents for the treatment of erectile dysfunctions (Merfort, Münch. Med. Wochenschr. 138 (1996), 504–507; Gomaa et al., Br. Med. J. 312 (1996), 1512–1515).

On the one hand, the hitherto known organic nitric acid esters have a number of associated therapeutic disadvantages. Thus, for example, it is necessary to observe the so-called nitrate tolerance, i.e. the decrease in the action of nitrate at high dosage or when administering longer-acting nitric acid esters. Side effects such as headache, vertigo, nausea, feeling of weakness, erythema and the danger of a comparatively large drop in blood pressure with reflex tachycardia have likewise been verified (Mutschler, Arzneimittelwirkungen (Drug actions), Wissenschaftliche Verlagsgesellschaft mbH, Stuttgart, 1991). On the other hand, PETN as an active substance possesses a number of outstanding properties, especially occurrence of the above-mentioned side effects to only a small extent, if at all, justifying the preferential use of this compound as a drug over other organic nitric acid esters (series of publications entitled "Pentaerythrityltetranitrat" ("Pentaerythrityl tetranitrate"), Dr. Dietrich Steinkopff Verlag, Darmstadt, 1994 to 1996).

The galenical processing of organic nitric acid esters to pharmaceutical formulations for the treatment of angina pectoris or ischaemic heart disease are generally known. It is carried out in accordance with the working procedures and rules generally familiar to those skilled in the art of pharmaceutics, the choice of which technologies to apply and which galenical adjuncts to use depending primarily on the active substance to be processed. Questions of its physicochemical properties, the chosen form of administration, the desired duration of action and the avoidance of drug/adjunct incompatibilities are of particular importance here. Especially peroral, parenteral, sublingual or transdermal administration, in the form of tablets, coated tablets, capsules, solutions, sprays or plasters, is described for drugs indicated for angina pectoris or ischaemic heart disease (DD-A5-293492, DE-AS-2623800, DE-OS-3325652, DE-OS-3328094, DE-PS-4007705, DE-OS-4038203, JP patent application 59/10513 (1982)).

A 1-alkyl-2-acetyl ether analogue of phosphatidylcholine of the formula

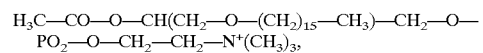

which is a platelet activation factor, is capable of inducing platelet aggregation and vasodilation even at an extremely low concentration of 0.1 nM in the blood (Stryer, Biochemie (Biochemistry), Spektrum der Wissenschaften, Heidelberg, 1990).

The possibility of using organic nitric acid esters as explosives has likewise been known for a long time (Ullmanns Encyklopädie der technischen Chemie (Ullmanns Encyclopaedia of Chemical Technology), vol. 16, 3rd edition, Urban & Schwarzenber, Munich-Berlin, 1965).

DESCRIPTION OF THE INVENTION

The object of the invention is to provide novel compounds derived from pentaerythritol which have pharmacologically advantageous actions, in particular with the greatest possible retention of the properties characteristic of pentaerythrityl tetranitrate and superior to those of other nitrates.

The object of the invention is achieved by compounds of general formula I:

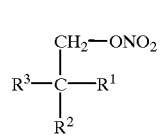

(I)

in which
- $R^1$, $R^2$, $R^3$ are identical to or different from one another and are $CH_2$—$ONO_2$, $CH_2$—$OR^4$ or $R^5$, at least one of the substituents $R^1$ to $R^3$ being $R^5$,
- $R^4$ is H or $C_1$- to $C_6$-alkanoyl,
- $R^5$ is $COR^6$,
- $R^6$ is OH, $OR^7$, $NH_2$, $NHR^7$, $NR^7{}_2$, $N^+R^7{}_3X$, $NR^8$, $NR^9R^{10}$, $NR^{11}R^{12}$ or NH—$NH_2$,
- $R^7$ is linear or branched $C_1$- to $C_6$-alkyl, linear or branched $C_1$- to $C_6$-alkenyl, aryl, aralkyl, heteroaryl or heteroaralkyl,
- $R^8$ is $C_1$- to $C_6$-alkylidene,
- $R^9$, $R^{10}$ are different from one another and are $R^7$,
- $R^{11}$, $R^{12}$ are identical to or different from one another and are $NR^7{}_2$, $N^+R^7{}_3X^-$ or $NR^8$, and
- X is a halogen or a group capable of anion formation, ps and therapeutically acceptable salts thereof.

$$(O_2NOCH_2)_2C(CH_2ONO_2)COR^6, \qquad (II)$$

$$(O_2NOCH_2)_2C(COR^6)_2, \qquad (III)$$

$$O_2NOCH_2C(COR^6)_3, \qquad (IV)$$

$$(O_2NOCH_2)_2C(CH_2OR^4)COR^6, \qquad (V)$$

$$(O_2NOCH_2)C(CH_2OR^4)_2COR^6 \text{ and} \qquad (VI)$$

$$(O_2NOCH_2)C(CH_2OR^4)(COR^6)_2, \qquad (VII)$$

or those in which
- $R^4$ is H or $C_1$- to $C_6$-alkenoyl, and
- $R^6$ is OH, $OR^7$, $NH_2$, $NHR^7$, $NR^7{}_2$ or $N^+R^7{}_3X^-$, i.e. especially the esters and mixed esters, amides, hemiamides, amidoesters and ammonium salts.

Other preferred embodiments are compounds having one, two and three hydrophilic groups. This relates in particular to the metal and ammonium salts, esters, amides and hydrazides of carboxylic acids. Particularly preferred compounds are those of formulae VIII to XIII:

$$(O_2NOCH_2)_2C(CH_2ONO_2)COOH, \qquad (VIII)$$

$$(O_2NOCH_2)_2C(COOH)_2, \qquad (IX)$$

$$O_2NOCH_2C(COOH)_3, \qquad (X)$$

$$(O_2NOCH_2)_2C(CH_2OH)COOH, \qquad (XI)$$

$$(O_2NOCH_2)C(CH_2OH)_2COOH \text{ and} \qquad (XII)$$

$$(O_2NOCH_2)C(CH_2OH)(COOH)_2, \qquad (XIII)$$

especially 3-nitryloxy-2,2-bis(nitryloxymethyl)propionic acid, 2,2-bis(nitryloxymethyl)malonic acid and 2-carboxy-2-nitryloxmethlmalonic acid.

The readily accessible nitric acid esters of pentaerythritol are used as starting compounds; for the preparation of said esters, reference is made expressly to the process of partial denitration of pentaerythrityl tetranitrate by means of hydrazine (Simecek, Coll. Czech. Chem. Comm. 27 (1962), 363 and U.S. Pat. No. 3,408,383). Another method is the nitration of pentaerythritol to the trinitrate, followed by its hydrazinolysis to pentaerythrityl dinitrate and mononitrate and by chromatographic separation of the mixture formed. Other starting compounds used are 2,2-bis(hydroxymethyl) malonic acid (Gault, Roesch, C. R. Hebd. Séances Acad. Sci. (1934), 615; Bull. Soc. Chim. Fr. <5>4 (1937), 1432) and 2-carboxy-2-hydroxymethylmalonic acid (Hueckel et al., Lieb. Ann. Chem. 528 (1937), 68). Further processing to the individual target compounds is carried out in each case by means of reactions and methods familiar to those skilled in the art. Thus, for example, acid-catalyzed reaction of nitryloxymethylated propionic or malonic acids or their acid halides with alcohols, or other esterification methods familiar to those skilled in the art, such as transesterifications, give the corresponding esters in good yields. Linear and branched primary, secondary and tertiary $C_1$–$C_6$-alkanols and -alkenols and aryl, heteroaryl, aralkyl and heteroaralkyl alcohols are particularly suitable for this purpose. The homologous acid amides, hemiamides or hydrazides are obtained by reacting said acid halides and esters with $NH_3$, primary and secondary amines or hydrazine or 1-substituted hydrazines. Primary and secondary aliphatic, aromatic and heteroaromatic amines or hydrazine and 1-substituted hydrazines are suitable for this purpose.

A further embodiment of the invention consists of the compounds of general formula XIV:

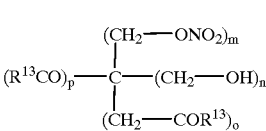

(XIV)

in which
$R^{13}$ is a group of formula XV:

(XV)

and
m to r are integers where:

$m+n+o+p=4,$ $q+r=3,$ m and/or $r \geq 1$ and
o and/or $p \geq 1$. 3-Nitryloxy-2,2-bis(nitryloxymethyl) propyl 3-nitryloxy-2,2-bis(nitryloxymethyl)propionate is a particularly preferred compound.

The compounds of formula XIV are obtained in particular from the compounds of formulae VIII to XIII, e.g. 3-nitryloxy-2,2-bis(nitryloxymethyl)propionic acid (Tri-PA), 2,2-bis(nitryloxymethyl)malonic acid (Bis-MA) or 2-carboxy-2-nitryloxymethylmalonic acid (CN-MA), by reaction with pentaeryth derivatives of formula XV.1:

$$HO—CH_2C(CH_2OH)_q(CH_2ONO_2)_r. \qquad (XV.1)$$

Likewise. derivatives of the compounds of formulae VIII to XIII, for example of Tri-PA, Bis-MA, CN-MA or XV.1, can be used as starting compounds for the synthesis of the compounds XIV, whose functional groups, as suitable leaving groups, enable those skilled in the art to have access to the target compounds via esterification reactions. The reaction is performed by the generally known methods and procedures for the preparation of esters.

Compounds of formulae VIII to XIII, for example Tri-PA, Bis-MA, CN-MA and derivatives thereof, are also suitable in analogous manner as acid components for the preparation of esters whose alcohol component is formed by a partially nitrated polyalcohol, especially isosorbide mononitrate, 1-nitroglycerol, 2-nitroglycerol, 1,2-dinitroglycerol, 1,3-dinitroglycerol or partially nitrated erythritols. These esters are likewise within the scope of the present invention.

Another embodiment of the invention consists of the compounds of general formula XVI:

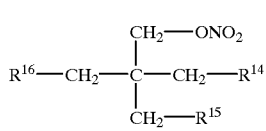

(XVI)

in which $R^{14}, R^{15}, R^{16}$ are identical to or different from one another and are H, $OR^{19}$, $ONO_2$, $OR^{17}$ or $R^{18}$, $R^{17}$ is $COR^{19}$ or $R^{23}$, $R^{18}$ is $O(PO_2H)OR^{20}$, $O(PO_2H)OR^{22}$, $OSO_2OR^{22}$ or $COOR^{19}$, $R^{19}$ is H or linear or branched $C_1$- to $C_6$-alkyl, $R^{20}$ is linear or branched $C_1$- to $C_6$-alkyl-$R^{21}$, $R^{21}$ is $NR^{19}{}_2$, $N^+R^{19}{}_3$ or $N^+R^{19}{}_3X^-$, $R^{22}$ is $R^{19}$, aryl or $NR^{19}{}_2$, $R^{23}$ is a 3- or 5-carbonyl radical of a 1,4-dihydropyridine-3,5-dicarboxylic acid optionally substituted in the 2-, 4- and/or 6-position, a 1-substituted pyrrolidine-2-carbonyl radical, an N-carbonyl radical of a substituted sydnone imine, a radical —CO—CH(NHCOR$^{19}$)—CR$^{19}{}_2$—S—NO, a radical —CO—CH(NH$_2$)—CR$^{19}{}_2$—S—NO or a radical —NH—CH(COOR$^{19}$)—CR$^{19}{}_2$—S—NO, and X is a halogen or a group capable of anion formation, and therapeutically acceptable salts thereof, with the exception of the following combinations:

$R^{14}=R^{15}=R^{16}=ONO_2$;

$R^{14}=OH$, $R^{15}=R^{16}=ONO_2$;

$R^{14}=R^{15}=OH$, $R^{16}=ONO_2$; and $R^{14}=R^{15}=R^{16}OH$.

The preferred compounds are those in which $R^{14}$ is $OR^{19}$ or $R^{18}$, $R^{15}, R^{16}$ are $ONO_2$, and $R^{18}$ is $COOR^{19}$, especially those of formula XVII:

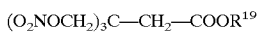

(XVII)

in which $R^{19}$ is H, methyl, ethyl, Na or K,
and those of formula XVIII:

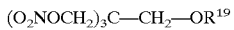

(XVIII)

in which $R^9$ is methyl or ethyl.

The readily accessible monobromopentaerythritol (Wawzonek et al., Org. Syntheses Coll. Vol. IV [1963] 681) and bis[2,2,2-tris(nitryloxymethyl)]ethyl ether (Friedrich et al., B. 63 [1930] 2683) are used as starting compounds. Further processing to the individual target compounds is carried out in each case by means of reactions and methods familiar to those skilled in the art. Thus there are 2 possible multistep synthetic routes to the preparation of 4-nitryloxy-3,3-bis(nitryloxymethyl)butanoic acid starting from monobromopentaerythritol. On the one hand, monobromopentaerythritol reacts in a nucleophilic substitution reaction to give 3,3-bis(hydroxymethyl)-4-hydroxybutyronitrile, which is saponified to 3,3-bis(hydroxymethyl)-4-hydroxybutanoic acid (Govaert et al., Mededeelingen van de Koninklijke Vlaamsche Academie voor Wetenschappen, Letteren en Schoone Kunsten van Belgie, Klasse der Wetenschappen 16 [1954] no. 8, 3–12) and then yields 4-nitryloxy-3,3-bis(nitryloxymethyl)butanoic acid on full esterification with nitric acid (U.S. Pat. No. 3,408,383). On the other hand, 4-nitryloxy-3,3-bis(nitryloxymethyl)butanoic acid is obtained by the esterification of monobromopentaerythritol with nitric acid to give 3-nitryloxy-2,2-bis(nitryloxymethyl)propyl bromide (D. E. Elrik et al., Am. Soc. 76[1954] 1374), followed by conversion to a Grignard reagent and reaction with carbon dioxide. Diethyl 2,2-bis(nitryloxymethyl) malonate is prepared using the readily accessible diethyl 2,2-bis(hydroxymethyl)malonate (Gault, Roesch, C. R. Hebd. Séances Acad. Sci. 199 (1934) 615). Methyl 2,2,2-tris(nitryloxymethyl)ethyl ether is obtained by WILLIAMSON's ether synthesis or by reacting pentaerythrityl trinitrate with an ether solution of diazomethane in the presence of catalytic amounts of boron trifluoride.

Another embodiment consists of the compounds in which the 3- or 5-carbonyl radical of a 1,4-dihydropyridine-3,5-dicarboxylic acid optionally substituted in the 2-, 4- and/or 6-position is formed by an unsymmetrical ester radical, the 1-substituted pyrrolidine-2-carbonyl radical is formed by a radical, or the N-carbonyl radical of a substituted sydnone imine is formed by a radical, said radicals being known by those skilled in the art to belong to the classes of substances comprising calcium antagonists, ACE inhibitors and coronary dilators.

The compounds of general formula XIX:

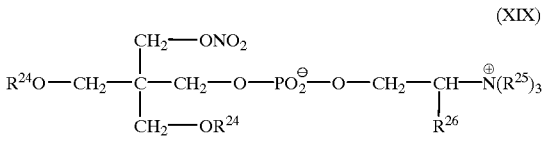

(XIX)

in which $R^{24}$ is H, $NO_2$, acyl, alkyl or alkenyl, $R^{25}$ is H or $CH_3$, and $R^{26}$ is H, represent another embodiment of the invention, the preferred compounds being those of formula XX:

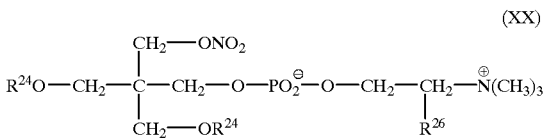

(XX)

and especially that of formula XXI:

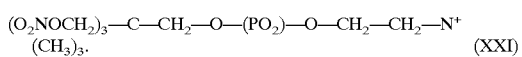

(XXI)

An additional embodiment of the present invention consists of the compounds of general formula XXII:

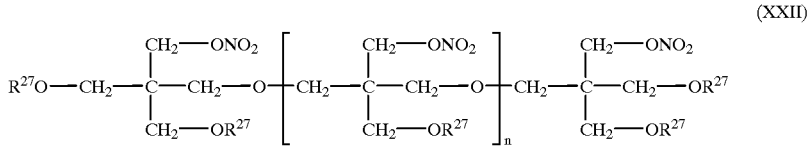

(XXII)

in which
R$^{27}$ independently of one another are NO$_2$ or R$^{17}$ to R$^{23}$, each of which is as defined above, and
n is an integer from 0 to 10, preferably from 0 to 4.
Preferred compounds are that of formula XXIII:

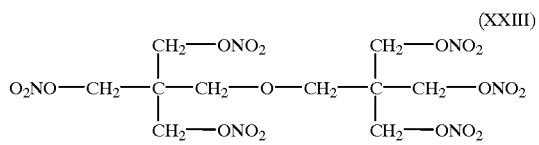

(XXIII)

that of formula XXIV:

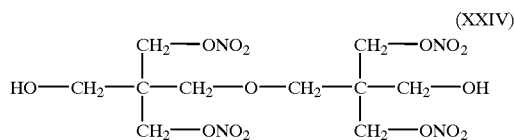

(XXIV)

and that of formula XXV:

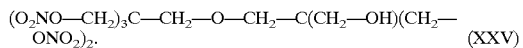

(XXV)

The symmetrical bis(2,2-bis(nitryloxymethyl)-2-hydroxymethyl)ethyl ether is prepared for example by the process of partial denitration of bis[2,2,2-tris-(nitryloxymethyl)]ethyl ether by means of hydrazine.

The compounds of general formula I in which R$^1$ to R$^5$ are as defined above and additionally at least one of the substituents R$^6$ is Cl or Br, especially the compounds 3-nitryloxy-2,2-bis(nitryloxymethyl)propionyl chloride, 2,2-bis(nitryloxymethyl)malonyl dichloride and 2-chlorocarbonyl-2-nitryloxymethylmalonyl dichloride, the compounds of general formula XIV in which additionally at least one of the substituents R$^{13}$ is Cl or Br and the compounds of general formula XVI in which R$^{14}$ to R$^{16}$ are as defined above and additionally at least one of the substituents R$^{18}$ is COCl or COBr represent inter alia useful intermediates in the synthesis of the target compounds described above.

Furthermore, it is obvious to those skilled in the art that, to prepare the compounds according to the invention, they can or must use a variety of derivatives in which reactive centres are inactivated by known protecting groups in order to avoid unwanted secondary reactions and by-products. These protecting groups can be removed after completion of the appropriate reaction or in the appropriate final step. The use of these derivatives which carry protecting groups is likewise within the scope of the present invention.

It is also possible to use pharmacologically acceptable derivatives of all the above-mentioned compounds. In particular, customary addition compounds, salts or enzymatically or hydrolytically cleavable compounds, such as esters, amides and the like, represent possible variations.

Depending on the process conditions and the starting materials, different end products are obtained as the free acid or base, base or acid addition salt or betaine, all of which are within the scope of the invention. Thus it is possible to obtain acid, basic, neutral or mixed salts and hydrates. On the one hand, the salts in question can be converted in a manner known per se to the free acid or base using appropriate reagents or by means of ion exchange. On the other hand, the free acids or bases obtained can form salts with organic or inorganic bases or acids. The bases used to prepare base addition salts are particularly those which form suitable therapeutically acceptable salts. Examples of such bases are alkali metal and alkaline earth metal hydroxides or hydrides, ammonia, amines and hydrazines or guanidines. Likewise, the acids used to prepare acid addition salts are preferably those which form suitable therapeutically acceptable salts. Examples of such acids are hydrohalic, sulfonic, phosphoric, nitric and perchloric acids, as well as aliphatic, acyclic, aromatic or heterocyclic carboxylic or sulfonic acids such as formic, acetic, propionic, succinic, glycolic, lactic, malic, tartaric, citric, gluconic, saccharic, glucuronic, ascorbic, maleic, hydroxymaleic, pyruvic, phenylacetic, benzoic, p-aminobenzoic, anthranilic, p-hydroxybenzoic, salicylic, acetylsalicylic, p-aminosalicylic, embonic, methanesulfonic, ethanesulfonic, hydroxyethanesulfonic, ethylenesulfonic, halogenobenzenesulfonic, toluenesulfonic, naphthylsulfonic or sulfanilic acid, and amino acids such as e.g. methionine, tryptophan, lysine or arginine. These and other salts of the novel compounds, e.g. picrates, can be used as a means of purifing the free acids or bases obtained. Salts of the acids or bases can be formed and separated out from solutions, after which the free acid or base can be obtained in a purer state from a new salt solution. Because of the relationship between the novel compounds in the free form and their salts, the salts are within the scope of the invention.

Depending on the choice of starting materials and process, some of the novel compounds can exist as optical isomers or as the racemate; alternatively, if they contain at least two centres of asymmetry, they can exist as an isomer mixture (racemate mixture). The isomer mixtures (racemate mixtures) obtained can be separated into two pure stereoisomeric (diastereoisomeric) racemates by means of chromatography or fractional crystallization. The racemates obtained can be separated by methods known per se, for instance by recrystallization from an optically active solvent, by the use of microorganisms, by reaction with optically active reagents to form compounds which can be separated, or by separation on the basis of the different solubilities of the diastereoisomers. Suitable optically active reagents are the L and D forms of tartaric, di-o-tolyltartaric, malic, mandelic, gluconic, saccharic, glucuronic, camphorsulfonic, quininic or binaphthylphosphoric acid, or optically active bases. It is preferable to isolate the more active moiety of the two antipodes. The starting materials are known or, if novel, can be obtained by methods known per se. The racemate mixtures and optically pure isomers, and their salts or addition compounds with optically active reagents, are likewise within the scope of the present invention.

The compounds according to the invention can be put to clinical use on their own or as part of a galenical preparation, either as the sole active substance, or in combination with one another, or combined with known cardiovascular therapeutic agents, for example ACE inhibitors, antiatherosclerotics, antihypertensives, beta-blockers, cholesterol depressants, diuretics, calcium antagonists, coronary dilators, lipid depressants, peripheral vasodilators, platelet aggregation inhibitors or other substances also used as cardiovascular therapeutic agents. Galenical formulations are prepared in accordance with the working procedures and rules generally familiar to those skilled in the art of pharmaceutics, the choice of which technologies to apply and which galenical adjuncts to use depending primarily on the active substance to be processed. Questions of its physicochemical properties, the chosen form of administration, the desired duration of action, the site of action and the avoidance of drug/adjunct incompatibilities are of particular importance here. Those skilled in the art are therefore responsible for selecting the medicinal form, adjuncts and preparative technology, in a manner which is trivial per se, with the aid of known substance and process parameters. The appropriate medicinal form should be designed so that, to achieve therapeutic plasma levels, it contains the active substance in question in an amount which makes it possible to divide the daily dose into 1 or 2 individual doses in the case of controlled release systems, or up to 10 individual doses in the case of other medicinal forms. Continuous administration by means of long-term infusion is also suitable. To achieve endothelium-protecting effects, it will generally be desirable to aim for sustained therapeutic blood levels. According to the invention, said compounds can particularly be administered orally, intravenously, parenterally, sublingually or transdermally. The medicinal formulation in question is preferably prepared in liquid or solid form. Suitable forms for this purpose are solutions, especially for the formulation of drops, injections, aerosol sprays or powder inhalers, as well as suspensions, emulsions, syrups, tablets, film-coated tablets, other coated tablets, capsules, pellets, powders, lozenges, implants, suppositories, creams, gels, ointments, plasters or other transdermal systems. The pharmaceutical formulations contain conventional organic or inorganic excipients and adjuncts usable for galenical purposes, which should themselves be chemically inert towards the active substances in question. This also includes chemical derivatization when the latter are brought into contact with excipients, relating especially to the formation of adducts with sugar derivatives like crosscarmelloses or cyclodextrins. Without implying a limitation, suitable pharmaceutical adjuncts are water, salt solutions, alcohols, vegetable oils, polyethylene glycols, gelatin, lactose, amylose, magnesium stearate, talcum, highly disperse silicon dioxide, paraffin, fatty acid monoglycerides and diglycerides, cellulose derivatives, polyvinylpyrrolidone and the like. The formulation can be sterilized and, if necessary, adjuncts like bulking agents, binders, formulation lubricants, mould release agents, mould lubricants, disintegrating agents, humectants, adsorbents, antidisintegrants, preservatives, stabilizers, emulsifiers, solubilizers, salts for influencing the osmotic pressure, buffer solutions, colours, fragrances, flavourings or sweeteners may be added. Using the appropriate substance parameters, those skilled in the art of pharmaceutics will have a suitable choice for avoiding drug/adjunct incompatibilities.

In contrast to many known organic nitric acid esters used in therapeutics, a number of the compounds described above are characterized by a surprising hydrophilicity, which makes their galenical processing possible for the first time, simpler or more reliable because, in particular, the use of organic solvents can be largely dispensed with in the manufacture of pharmaceutical preparations, so they are also particularly suitable in general for use in sprays and metered aerosols, as well as solutions. Said good to very good water solubility moreover increases their absorption, ultimately leading to an improved bioavailability.

It has also been found that, surprisingly, the compounds according to the invention have the desired properties. Furthermore, some of them are characterized by an optimized NO release, e.g. by their differentiated content of reductively or oxidatively biotransforming NO precursor groups or by an improved or increased multiphase NO release, and, depending on the intended use, by increased lipophilicity or hydrophilicity, good bioavailability and increased cGMP accumulation, and by pharmacodynamic preload reduction, reduced increase in plasma endothelin, pronounced platelet aggregation inhibition due to platelet-active groups, and endothelium-protecting action.

The described invention thus opens up improved and considerably expanded therapeutic possibilities for the treatment of pathological situations such as cardiac and vascular diseases, especially coronary heart disease, vascular stenoses and circulatory disorders of the peripheral arteries, hypertonia, microangiopathies and macroangiopathies in the context of diabetes mellitus, atherosclerosis, oxidative stress conditions in vessels and tissues, including the secondary diseases resulting therefrom, erectile dysfunctions, increased intraocular pressure, dysmenorrhoea, dysfunctional uterine bleeding, uterine contractility dysfunctions such as premature labour, menopausal symptoms or incontinence.

The Examples which follow will illustrate the invention in greater detail in respect of its nature and its implementation, without however limiting its scope.

EXAMPLES

Example 1

Pentaerythrityl trinitrate 158 g (0.5 mol) of pentaerythrityl tetranitrate (PETN) are dissolved in a boiling mixture of 300 ml of dioxane and 300 ml of ethanol, and different amounts of aqueous hydrazine hydrate solution (1.5–4 mol) are added in portions over 1 hour. The reaction mixture is then refluxed for a further 2.5 hours. The solvents are evaporated off at 15 mm Hg and the residue is extracted by shaking several times with 100 ml portions of water, as required, until the volume of the oil layer no longer decreases on extraction. The aqueous extracts (A) are collected and the residual oily layer is dissolved in twice its volume of ethanol. Any white precipitate of PETN which has separated out is filtered off after 24 hours; m.p.=132° C., nitrogen content: 17.35%; m.p.=141° C. (2×acetone); nitrogen content: conforms. Ethanol is evaporated off from the filtrate at 15 mm Hg. The viscous oily residue consists of crude pentaerythrityl trinitrate (PETriN); nitrogen content: conforms.

Example 2

Pentaerythrityl dinitrate and pentaerythrityl mononitrate

The combined aqueous extracts A of Example 1 are extracted by shaking three times with ether, the ether layer is separated from the aqueous layer B and dried over anhydrous $Na_2SO_4$ and the ether is evaporated off. The very viscous, oily evaporation residue consists of crude pentaerythrityl dinitrate (PEDN). The aqueous fraction B, which contains denitration products, mainly hydrazine nitrite, together with pentaerythrityl mononitrate (PEMN) and pentaerythritol, is acidified successively with 2 N $H_2SO_4$ until the evolution of gas ($N_2$, $N_2O$, NO, $N_3H$) has ceased, and is then concentrated at 20 mm Hg until solid products start to separate out, and extracted with ether. The crystalline substance of m.p. 62° C. which remains after evaporation of the ether is crude PEMN. This is then washed with cold chloroform and recrystallized from chloroform. M.p.=79° C. ($HCCl_3$); nitrogen content: conforms.

Example 3
Pentaerythrityl trinitrate-acetate and pentaerythrityl dinitrate-diacetate A mixture of 50 ml of acetic anhydride and 20 ml of acetyl chloride is added in portions, with cooling and stirring, to 135.5 g (0.5 mol) of crude PETriN [or 56.5 g (0.25 mol) of PEDN]. The mixture which has solidified after the reaction is stirred twice with 50 ml of ethanol and filtered off with suction. Colourless crystals are obtained in both cases.
Pentaerythrityl trinitrate-acetate (PETriNAc): m.p.=89° C. (2×ethanol); yield:

77%; nitrogen content: conforms.
Pentaerythrityl dinitrate-diacetate (PEDNdAc): m.p.=47° C. (2×ethanol); yield:

72%; nitrogen content: conforms.

Example 4
Pentaerythrityl trinitrate and pentaerythrityl dinitrate 104.4 g (0.3 mol) of PETriNAc or 51.7 g (0.15 mol) of PEDNdAc are dissolved in 400 ml of hot ethanol, a solution of 1.5 g of NaOH in 50 ml of ethanol is added and the azeotropic ethanol/ethyl acetate mixture (b.p.$_{760}$=71.8° C.) is distilled off. When the formation of ethyl acetate has ended, a further 1.5 g of NaOH in 50 ml of ethanol are added and fractionation is continued until no more ethyl acetate passes over. The ethanol is then evaporated off at 15 mm Hg and the residue is extracted by shaking three times with 20 ml of water in the case of PETriN and stirred with 100 ml of water and extracted three times with ether in the case of PEDN. After drying under vacuum or removal of the ether, the pure substances, PETriN and PEDN, remain as colourless viscous liquids, which are dried under vacuum over $P_2O_5$.
PETriN: nitrogen content: conforms.
PEDN: nitrogen content: conforms.

Example 5
Pentaerythrityl trinitrate ⅓$H_2O$

PETriN obtained according to Example 4 is washed with water, then stirred with 100 ml of water and then left to stand until the next day at a temperature not exceeding 20° C. After suction filtration and drying, air-stable colourless crystals are obtained. M.p.=32° C.; water content (Karl-Fischer method): conforms after drying under vacuum at 60° C.

Example 6
Pentaerythrityl trinitrate

PETriN is prepared by nitrating pentaerythritol with $HNO_3$ (95%) in the presence of urea.

Example 7
Pentaerythrityl dinitrate and pentaerythrityl mononitrate
PEDN and PEMN are prepared from PETriN by hydrazinolysis (4 mol of $NH_2NH_2$ (50%)) and then separation of the 1:1 mixture by column chromatography.

Example 8
3-Nitryloxy-2,2-bis(nitryloxymethyl)propionic acid 0.0074 mol of $KMnO_4$ is added in portions, with vigorous stirring, to a solution of 0.0037 mol of pentaerythrityl trinitrate (PETriN), 5.5 ml of benzene, 9 ml of water and 0.15 ml of Aliquat® 336. When the addition has ended, the temperature is kept at 15° C. for 2 hours. Aqueous hydrogensulfite solution is then added, the mixture is acidified with $H_2SO_4$ and the benzene layer is separated off. After removal of the solvent, 3-nitryloxy-2,2-bis(nitryloxymethyl) propionic acid (Tri-PA) is obtained as a solid residue, which is recrystallized several times from methylene chloride. Yield: 72%.

$R_f$=0.32 (hexane/ethyl acetate/glacial acetic acid=5:5:1); m.p.=112° C. ($CH_2Cl_2$);
solubility:
  readily soluble in: water, methanol, acetone;
  sparingly soluble in: toluene, methylene chloride, chloroform;
  insoluble in: hexane;
  elemental analysis: (C: conforms, H: conforms, N: conforms);
$^1$H NMR (300 MHz, $(CD_3)_2CO$): conforms; $^{13}$C NMR (75 MHz, $(CD_3)_2CO$): conforms; MS (70 eV): m/z (%): conforms.

Example 9
3-Nitryloxy-2,2-bis(nitryloxymethyl)propionic acid 0.02 mol of PETriN is added dropwise at 25° C. to 6.5 ml of 70% $HNO_3$. The mixture is left to stand for 18 hours at 25° C. and then heated for 3 hours at 70° C. It is then evaporated to dryness and the residue (Tri-PA) is recrystallized from chloroform. Yield: 52%. Elemental analysis: (C: conforms, H: conforms, N: conforms).

Example 10
3-Nitryloxy-2,2-bis(nitryloxymethyl)propionic acid

A porous pot is suspended in a glass beaker as a diaphragm. 25% $H_2SO_4$ is used as the catholyte. The cathode consists of lead; a lead plate, as the anode, dips in the anolyte solution, which consists of 0.0275 mol of PETriN, 500 ml of 60% $H_2SO_4$ and 10 g of chromium(VI) oxide. When the electrolysis has ended, the reaction mixture is extracted with ether and the ether is removed to leave Tri-PA as a dirty-white crystalline mass, which is recrystallized from chloroform. Yield: 60%. Elemental analysis: (C: conforms, H: conforms, N: conforms).

Example 11
3-Nitryloxy-2,2-bis(nitryloxymethyl)propionic acid 1 g of cobalt(II) chloride is added at 45–50° C., with stirring, to a solution of 0.095 mol of PETriN and 4.2 g of NaOH in 150 g of 10% sodium hypochlorite solution. After 5 hours, the mixture is filtered and the filtrate is extracted with ether and acidified with concentrated hydrochloric acid. The acid solution is extracted with ether and the ether is evaporated off. The crude crystalline mass of Tri-PA is recrystallized from water. Yield: 70%. Elemental analysis: (C: conforms, H: conforms, N: conforms).

Example 12
3-Nitryloxy-2,2-bis(nitryloxymethyl)propionic acid 0.042 mol of PETriN is refluxed for 20 hours in 30 ml of pyridine containing 0.084 mol of selenium dioxide. The deposit of selenium is separated off and the filtrate is steam-distilled. The aqueous residue is extracted with ether and the ether is evaporated off. The oily residue of Tri-PA is

Example 13
2,2-Bis(nitryloxymethyl)malonic acid and 2-carboxy-2-nitryloxymethylmalonic acid 1.0 g (0.0061 mol) of 2,2-bis(hydroxymethyl)malonic acid or 0.004 mol of carboxy-2-hydroxymethylmalonic acid is added, with stirring and ice-cooling, to a mixture, cooled to 0° C., of 2.5 g of 95% $HNO_3$, a spatula tipfull of urea and 10 ml of water. After 10 minutes, 2.5 g of 94% $H_2SO_4$ are added dropwise, with stirring, and stirring is continued for one hour at 0C. The organic layer is separated off and evaporated to give a residue of 2,2-bis(nitryloxymethyl) malonic acid or 2-carboxy-2-nitryloxymethylmalonic acid as a viscous oil, which is purified by column chromatography. Yield: 45% or 30%. Elemental analysis: (C: conforms, H: conforms, N: conforms).

Example 14
Sodium and potassium 3-nitryloxy-2,2-bis(nitryloxymethyl) propionate 1.0 g (0.0032 mol) of Tri-PA is dissolved in 30 ml of water. The solution is titrated to pH 7 with 1% aqueous sodium or potassium hydroxide solution using a pH measuring electrode. Evaporation of the aqueous solution leaves the white sodium or potassium salt of Tri-PA, which is recrystallized from a small volume of water. Yield: 87% in each case.

Tri-PA sodium salt:
  elemental analysis: (C: conforms, H: conforms, N: conforms). Tri-PA potassium salt:
  elemental analysis: (C: conforms, H: conforms, N: conforms).

Example 15
Sodium 3-nitryloxy-2,2-bis(nitryloxymethyl)propionate 7 mmol of Tri-PA are dissolved in 10 ml of water. The acid solution is adjusted to pH 7 with 1% aqueous sodium hydroxide solution and evaporated over several days at room temperature to induce slow crystal growth. Yield: 85%. M.p.=310–311° C. ($H_2O$). Elemental analysis: (C: conforms, H: conforms, N: conforms).

Example 16
3-Nitryloxy-2,2-bis(nitryloxymethyl)propionyl chloride 1 g (3.5 mmol) of Tri-PA is refluxed for 1.5 hours with 5.3 mmol of thionyl chloride. The excess thionyl chloride is distilled off, first in a water bath and then under vacuum. The residue is taken up in diethyl ether and washed rapidly with a small volume of ice-water. The organic phase is separated off and dried over sodium sulfate and the solvent is evaporated off under vacuum. The oily 3-nitryloxy-2,2-bis(nitryloxymethyl)propionyl chloride (Tri-PACl) obtained is sufficiently pure for further reactions. Yield: 75%. Elemental analysis: (C: conforms, H: conforms, N: conforms).

Example 17
2,2-Bis(nitryloxymethyl)malonyl dichloride and 2-chlorocarbonyl-2-nitryloxy-methylmalonyl dichloride The acid chlorides of the compounds 2,2-bis(nitryloxymethyl)malonic acid (Bis-MA) and 2-carboxy-2-nitryloxymethylmalonic acid (CN-MA) are obtained analogously to Example 10. The preparation of 2,2-bis(nitryloxymethyl)malonyl dichloride (Bis-MADCl) uses twice the amount of thionyl chloride and the preparation of 2-chlorocarbonyl-2-nitryloxymethylmalonyl dichloride (CN-MATriCl) uses three times the amount of thionyl chloride. Yield: 70 or 45%.

Bis-MADCl:
  elemental analysis: (C: conforms, H: conforms, N: conforms).
CN-MATriCl:
  elemental analysis: (C: conforms, H: conforms, N: conforms).

Example 18
Methyl 3-nitryloxy-2,2-bis(nitryloxymethyl)propionate 1 ml of thionyl chloride and 1 drop of dry DMF are added to 7 mmol of Tri-PA and the mixture is stirred for 20 min at room temperature with the exclusion of moisture. Excess thionyl chloride is then distilled off, the reaction mixture is cooled to 0° C. and 10 ml of dry methanol are added. After 30 min, the mixture is diluted with 30 ml of water and extracted five times with diethyl ether. The crude product obtained after evaporation of the solvent is purified by column chromatography (hexane/ethyl acetate=2:1) to give methyl 3-nitryloxy-2,2-bis(nitryloxymethyl)propionate (Tri-PA methyl ester) as colourless crystals. Yield: 44%. M.p.=66° C. Elemental analysis: (C: conforms, H: conforms, N: conforms).

Example 19
Ethyl 3-nitryloxy-2,2-bis(nitryloxymethyl)propionate 10.5 mmol of ethanol, 20 mg of toluenesulfonic acid and 30 ml of chloroform are added to 1 g (3.5 mmol) of Tri-PA and the mixture is refluxed for 12 hours with a water separator. The chloroform phase is washed with aqueous bicarbonate solution and with water, the solvent is evaporated off under vacuum and the residue is purified by column chromatography to give ethyl 3-nitryloxy-2,2-bis-(nitryloxymethyl)propionate (Tri-PA ethyl ester) as a colourless oil. Yield: 85%. Elemental analysis: (C: conforms, H: conforms, N: conforms).

Example 20
Butyl 3-nitryloxy-2,2-bis(nitryloxymethyl)propionate 1 ml of n-butanol is dissolved in 5 ml of pyridine, and a solution of 0.5 g (1.7 mmol) of Tri-PACl (cf. Ex. 10) in 5 ml of tetrahydrofuran is added, with ice-cooling. The mixture is heated for 1 hour in a water bath. It is then poured into 50 ml of ice-water and neutralized carefully with hydrochloric acid. The ester which has separated out as an oil is taken up in diethyl ether and washed with aqueous sodium carbonate solution and with water, the organic phase is dried over sodium sulfate and the solvent is evaporated off under vacuum. Purification of the residue by column chromatography . . . butyl 3-nitryloxy-2,2-bis(nitryloxymethyl) propionate (Tri-PA butyl ester) as a colourless oil. Yield: 69%. Elemental analysis: (C: conforms, H: conforms, N: conforms).

Example 21
Diethyl 2,2-bis(nitryloxymethyl)malonate 0.015 mol of diethyl 2,2-bis(hydroxymethyl)malonate is added slowly at −5° C., under a stream of air, to a solution of 90 g of degassed 100% nitric acid. Air is passed through the reaction mixture for a further 120 min at −5° C. and the mixture is then poured into ice-water. The aqueous phase is extracted twice with ether, the organic phase is washed with 10% hydrogencarbonate solution and with water and dried over sodium sulfate and the solvent is evaporated off under vacuum. The residue (Bis-MA diethyl ester) is separated by column chromatography. Yield: 94%. $R_f$=0.52 (silica gel, hexane/ethyl acetate=2:1). $^1$H NMR (300 MHz, $CDCl_3$): conforms; $^{13}$C NMR (75 MHz, $CDCl_3$): conforms.

Example 22

The esters of the carboxylic acid CN-MA are obtained analogously to Examples 18 to 21 by increasing the added reagents by the appropriate factor.

Example 23
3-Nitryloxy-2,2-bis(nitryloxymethyl)propionamide 1 g (3.4 mmol) of Tri-PACl is dissolved in 25 ml of dioxane, and excess concentrated ammonia solution is added. After 30 min, the mixture is poured into 100 ml of ice-water and weakly acidified with dilute hydrochloric acid. The oily 2,2-bis(nitryloxymethyl)-3-nitryloxypropionamide (Tri-PA amide) which has separated out is purified by column chromatography. Yield: 65%. Elemental analysis: (C: conforms, H: conforms, N: conforms).

Example 24
3-Nitryloxy-2,2-bis(nitryloxymethyl)propionamide 1 ml of thionyl chloride and 1 drop of dry DMF are added to 7 mmol of Tri-PA and the mixture is refluxed for 1.5 h with the exclusion of moisture. 3 ml of cold concentrated $NH_3$ solution are then added to the reaction mixture and the solution is left to cool to room temperature. Extraction of the aqueous phase five times with diethyl ether and removal of the solvent gives an oily crude product from which 3-nitryloxy-2,2-bis(nitryloxymethyl)propionamide (Tri-PA amide) are isolated as colourless crystals by means of column chromatography (hexane/ethyl acetate=1:1). Yield: 32%. $R_f$=0.52 (silica gel, hexane/ethyl acetate=1:1). M.p.=71–72° C. ($CHCl_3$). Elemental analysis: (C: conforms, H: conforms, N: conforms). $^1H$ NMR (300 MHz, $(CD_3)_2CO$): conforms; $^{31}C$ NMR (75 MHz, $(CD_3)_2CO$): conforms.

Example 25
3-Nitryloxy-2,2-bis(nitryloxymethyl)propionic acid N-benzylamide 1 g (3.5 mmol) of methyl 3-nitryloxy-2,2-bis (nitryloxymethyl)propionate is heated for 3 hours at 130° C. with 3 ml of benzylamine and 100 mg of ammonium chloride and the mixture is cooled, taken up in 50 ml of chloroform and washed successively with water, with dilute hydrochloric acid, with aqueous bicarbonate solution and again with water. The crude product obtained after evaporation of the solvent is purified by column chromatography to give 3-nitryloxy-2,2-bis(nitryloxymethyl)propionic acid N-benzylamide (Tri-PA-NBzl amide) as a colourless oil. Yield: 73%. Elemental analysis: (C: conforms, H: conforms, N: conforms).

Example 26
3-Nitryloxy-2,2-bis(nitryloxymethyl)propionic acid hydrazide 1 g (3.5 mmol) of methyl 2,2-bis(nitryloxymethyl)-3-nitryloxypropionate is heated for 5 hours in a water bath with excess aqueous hydrazine hydrochloride solution. The mixture is poured onto ice and weakly acidified with hydrochloric acid. The oil which has deposited is separated by column chromatography to give 3-nitryloxy-2,2-bis (nitryloxymethyl)propionic acid hydrazide (Tri-PA hydrazide) as a colourless oil. Yield: 63%. Elemental analysis: (C: conforms, H: conforms, N: conforms).

Example 27

The amides or hydrazides of the carboxylic acids Bis-MA and CN-MA are prepared analogously to Examples 23 and 26 by doubling or trebling the reagents.

a) Bis-MA diamide
  elemental analysis: (C: conforms, H: conforms, N: conforms).
b) Bis-MA dihydrazide
  elemental analysis: (C: conforms, H: conforms, N: conforms).
c) CN-MA triamide
  elemental analysis: (C: conforms, H: conforms, N: conforms).
d) CN-MA trihydrazide
  elemental analysis: (C: conforms, H: conforms, N: conforms).

Example 28
3-Nitryloxy-2,2-bis(nitryloxymethyl)propyl 3-nitryloxy-2,2-bis(nitryloxymethyl)-propionate 1 ml of thionyl chloride and 1 drop of dry DMF are added to 7 mmol of Tri-PA and the mixture is stirred for 20 min at room temperature with the exclusion of moisture. A solution of 7 mmol of PETriN in 7 mmol of pyridine is then added and the reaction mixture is stirred for 3 h at 70° C. The yellow solution is cooled to 0° C. and ice-water is added carefully. Extraction of the aqueous phase five times with diethyl ether and removal of the solvent gives a yellow oil from which 3-nitryloxy-2,2-bis(nitryloxymethyl)propyl 3-nitryloxy-2,2-bis(nitryloxymethyl)propionate (Tri-PA-PETriN ester) is separated by column chromatography (hexane/ethyl acetate=1:1). Yield: 24%. $R_f$=0.63 (silica gel, hexane/ethyl acetate=1:1). Elemental analysis: (C: conforms, H: conforms, N: conforms). $^1H$ NMR (300 MHz, $CDCl_3$): conforms; $^{13}C$ NMR (75 MHz, $CDCl_3$): conforms.

Example 29
2,2-Bis(hydroxymethyl)-3-hydroxypropyl bromide 200 g (1.47 mol) of pentaerythritol (PE), 1.5l of glacial acetic acid and 17 ml of 48% HBr are refluxed for 1.5 h. A further 170 ml of 48% HBr are added and the reaction mixture is then boiled for another 3 h. The same procedure is repeated with the addition of 96 ml of HBr. The glacial acetic acid and water are then distilled off completely, 750 ml of 98% ethanol and 50 ml of 48% HBr are added to the viscous residue and approx. 500 ml of ethanol are removed by slow distillation. A further 750 ml of ethanol are subsequently added and then distilled off completely. After the addition of 500 ml of toluene, the solvent is distilled off and the same procedure is repeated. The viscous residue is boiled for several hours with 500 ml of dry ether, with stirring, until a white solid deposits. The solid is filtered off with suction, washed with dry ether, dried and recrystallized from chloroform/ethyl acetate=3:2. Yield: 50%. M.p.=75–76° C.

Example 30
3,3-Bis(hydroxymethyl)-4-hydroxybutyronitrile 0.07 mol of KCN is added to 0.055 mol of 2,2-bis (hydroxymethyl)-3-hydroxypropyl bromide and the mixture is dissolved in 50 ml of acetonitrile and refluxed for 5 h, with stirring. After the solution has cooled, the solid is filtered off with suction and the mother liquor is concentrated. The residue is dissolved in chloroform, the residual KBr is separated off and the solvent is distilled off after drying. The desired nitrile is separated from the residue as a pale yellowish oil by column chromatography. Yield: 78%.

Example 31
3,3-Bis(hydroxymethyl)-4-hydroxybutanoic acid 25 ml of $Ba(OH)_2$ (T=0.62) are added to 2.0 g of 3,3-bis(hydroxymethyl)-4-hydroxybutyronitrile and the mixture is refluxed for 30 min until the evolution of ammonia has ceased. 50 ml of water are then added and the water is distilled off completely. The barium salt of the acid is recrystallized from water/ethanol. 0.005 mol of the salt is dissolved in a small volume of water, and 6.5 ml of sulfiric acid (0.9 N) are added, with stirring. The precipitate of barium sulfate is centrifuged off, the water is distilled off and the residue is recrystallized from ethanol. Yield: 60%.

Example 32
3-Nitryloxy-2,2-bis(nitryloxymethyl)propyl bromide 0.4 g of urea is added at 30° C. to 37 ml of 95% nitric acid and air is passed through the mixture for 5 min. The solution is then cooled to 0° C. and 85 ml of methylene chloride and 20 g of 2,2-bis(hydroxymethyl)-3-hydroxypropyl bromide are added, with stirring. 55 g of 94% sulfuric acid are then slowly added dropwise and the solution is stirred for a further one hour. The organic layer is separated off and dried and the solvent is removed. Recrystallization of the crude crystals from ethanol gives 3-nitryloxy-2,2-bis(nitryloxymethyl)propyl bromide. Yield: 62%. M.p.=90° C.

Example 33
3-Nitryloxy-2,2-bis(nitryloxymethyl)propyl bromide 0.015 mol of 2,2-bis(hydroxymethyl)-3-hydroxypropyl bromide is added slowly at −5° C., under a stream of air, to a solution of 90 g of degassed 100% nitric acid. Air is passed through the reaction mixture for a further 120 min at −5° C and the mixture is then poured into ice-water. The product which has precipitated out is filtered off, washed with water or 5% sodium hydrogencarbonate solution and then recrystallized from ethanol. Yield: 91%.

Example 34
4-Nitryloxy-3,3-bis(nitryloxymethyl)butanoic acid 0.4 g of urea is added at 30° C. to 37 ml of 95% nitric acid and air is passed through the mixture for 5 min. The solution is then cooled to 0° C. and 85 ml of methylene chloride and 0.1 mol of 3-bis(hydroxymethyl)-4-hydroxybutanoic acid are added, with stirring. 55 g of 94% sulfuric acid are then slowly added dropwise and the solution is stirred for a further one hour. The organic layer is separated off and extracted with 5% sodium hydroxide solution, the aqueous solution is acidified with dilute hydrochloric acid and extracted with methylene chloride and the solvent is dried and distilled off. 4-Nitryloxy-3,3-bis(nitryloxymethyl)butanoic acid (Tri-BA) is obtained after recrystallization from ethanol. Yield: 65%. Elemental analysis: (C: conforms, H: conforms, N: conforms).

Example 35
4-Nitryloxy-3,3-bis(nitryloxymethyl)butanoic acid

An ether solution of 2,2,2-tris(nitryloxymethyl) ethylmagnesium bromide is prepared by reacting a solution of 34 g of 3-nitryloxy-2,2-bis(nitryloxymethyl)propyl bromide in 60 ml of dry diethyl ether with 2.5 g of magnesium turnings in an ultrapure nitrogen atmosphere. Excess magnesium turnings are removed from the solution by filtration through a glass wool plug and the filtrate is transferred to a dropping funnel. The Grignard solution is then added dropwise over 15 min to a suspension of 150 g of finely powdered carbon dioxide in 60 ml of anhydrous diethyl ether. After one hour, the excess carbonic acid is evaporated off. The mixture is then acidified with 40 ml of cold 6 N hydrochloric acid and the 4-nitryloxy-3,3-bis(nitryloxymethyl)butanoic acid (Tri-BA) is extracted from the ether phase with dilute aqueous ammonia. The addition of further acid gives the product. Yield: 55%. Elemental analysis: (C: conforms, H: conforms, N: conforms).

Example 36
Methyl 4-nitryloxy-3,3-bis(nitryloxymethyl)butanoate

A 5-fold excess of thionyl chloride is added to 2.0 g of Tri-BA and the mixture is stirred at room temperature for 30 minutes. The excess thionyl chloride is distilled off and the residue is stirred under reflux for 30 minutes with a 10-fold excess of methanol. Water is added, with cooling, and the reaction mixture is extracted several times with diethyl ether. Drying and removal of the solvent leaves an oily residue containing 51% of methyl 4-nitryloxy-3,3-bis(nitryloxymethyl)butanoate (Tri-BA methyl ester). Elemental analysis: (C: conforms, H: conforms, N: conforms).

Example 37
Sodium and potassium 4-nitryloxy-3,3-bis(nitryloxymethyl)butanoate 1.0 g of Tri-BA is dissolved in 30 ml of water. The solution is titrated to pH 7 with 1% aqueous sodium or potassium hydroxide solution using a pH measuring electrode. Evaporation of the aqueous solution leaves the white sodium or potassium salt of Tri-BA, which is recrystallized from a small volume of water. Yield: 90% in each case.
Tri-BA sodium salt:
 elemental analysis: (C: conforms, H: conforms, N: conforms).
Tri-BA potassium salt:
 elemental analysis: (C: conforms, H: conforms, N: conforms).

Example 38
Methyl 2,2,2-tris(nitryloxymethyl)ethyl ether 0.025 mol of sodium and 0.12 mol of absolute methanol are used to prepare the methylate solution. 0.02 mol of 3-nitryloxy-2,2-bis(nitryloxymethyl)propyl bromide is added and the mixture is refluxed for 5 hours, with stirring and with the exclusion of moisture. After cooling, the reaction mixture is added to 5 times the amount of water and the ether (Me-PETriN ether) is separated off, washed again with water, dried and purified by column chromatography. Yield: 75%. Elemental analysis: (C: conforms, H: conforms, N: conforms).

Example 39
Methyl 2,2,2-tris(nitryloxymethyl)ethyl ether 0.02 mol of PETriN is dissolved in methanol/water (10:1), with the addition of catalytic amounts of boron trifluoride, and an ether solution of diazomethane is added at room temperature, with stirring, until a pale yellow colouration persists or until the evolution of $N_2$ has ceased. The solvent is distilled off and the residue is taken up with diethyl ether. This is then washed with dilute sodium hydroxide solution and with water and dried, the solvent is distilled off and the crude product (Me-PETriN ether) is purified by column chromatography. Yield: 49%. Elemental analysis: (C: conforms, H: conforms, N: conforms).

Example 40
Bis[2,2,2-tris(nitryloxymethyl)]ethyl ether 7 mmol of PETriN are heated at 50° C. for 30 min with 7 mmol of thionyl chloride and a 10-fold excess of pyridine in a water bath, with stirring. The solution is cooled to 0° C., the yellow crystalline mass is separated off and dissolved in diethyl ether and the pyridine is completely removed by multiple extraction with aqueous hydrochloric acid. The ether is removed to leave a viscous yellow oil, this is dissolved in chloroform and white crystals of bis[2,2,2-tris(nitryloxymethyl)]ethyl ether (Bis-PETriN ether) precipitate out slowly. Yield: 76%. M.p.=78° C. Elemental analysis: (C: conforms, H: conforms, N: conforms).

Example 41

Bis[2,2,2-tris(nitryloxymethyl)]ethyl ether

The product is obtained by slowly adding dipentaerythritol to nitric acid of specific gravity 1.52, taking care to ensure good water cooling and stirring. When the addition has ended, ⅔ of the liquid volume of concentrated sulfuric acid are added and some of the nitrate is precipitated out. When the nitration has ended, stirring is continued for 15 min. The reaction mixture is carefully poured into ice-water to complete the precipitation. Recrystallization from ethanol gives the product, Bis-PETriN ether, in pure form. Yield: 97%. M.p.=75° C.

Example 42

Bis(2,2-bis(nitryloxymethyl)-2-hydroxymethyl)ethyl ether 0.0167 mol of Bis-PETriN ether is dissolved in a boiling mixture of 10 ml of dioxane and 10 ml of ethanol, and 4.2 g of 25% aqueous hydrazine solution are added in portions over 30 min. The reaction mixture is refluxed for a further 2 h. After the reaction, the solvent is distilled off, the residue is dissolved in diethyl ether and dried and the ether is removed. Bis(2,2-bis(nitryloxymethyl)-2-hydroxymethyl) ethyl ether (Bis-PEDN ether) is separated from the oily crude product by column chromatography. Yield: 52%. Elemental analysis: (C: conforms, H: conforms, N: conforms).

Example 43

Study of the pharmacological action of the compounds:

a) The study is performed on cultivated cells (RFL-6 fibroblasts, LLC-PK1 epithelial cells), which are known as a model for characterizing the action and tolerance profiles of NO donors (Bennett et al., J. Pharmacol. Ther. 250 (1989), 316; Schröder et al., J. Appl. Cardiol. 2 (1987), 301; J. Pharmacol. Exp. Ther. 245 (1988), 413; Naunyn Schmiedeberg's Arch. Pharmacol. 342 (1990), 616; J. Pharmacol. Exp. Ther. 262 (1992), 298; Adv. Drug Res. 28 (1996), 253). The intracellular accumulation of cGMP as a parameter of the nitrate action and bioactivation is measured by means of a radioimmunoassay. The intracellular accumulation of cGMP brought about by the tested compounds is two to ten times higher than that of GTN or ISMN.

b) The platelet aggregation inhibiting action and thrombogenesis inhibiting action of the compounds is determined by the method of Rehse et al. (Arch. Pharm. 324, 301–305 (1991); Arch. Pharm. Pharm. Med. Chem. 329, 83 (1996), 191 (1996), 511 (1996)), which is established as a model especially of the extended Born test (Mackie et al., J. Clin. Pathol. 37 (1984), 874; Sharp et al., Thromb. Haem. 64(2) (1990), 211) for describing anticoagulant and antithrombotic properties. It is also determined by means of direct inhibition of the platelet function by organic nitrates and their biotransformation (Weber et al., Europ. J. Pharmacol.— Molecular Pharmacol. 247 (1993), 29; Weber et al., Europ. J. Pharmacol. 309 (1996), 209).

c) The endothelium-protecting action of the compounds is determined by the method of Noack and Kojda described in DE-A1-44 10 997.

d) Studies on the action against erectile dysfunctions are carried out by the method of Merfort et al. (Münch. Med. Wochenschrift 138 (1996), 504) and Gomaa et al. (Br. Med. J. 312 (1996), 1512).

e) To test the vasodilating properties, the substances were used in experiments on isolated rabbit aortic rings (H üisgen, Noack, Kojda: Int. Confer. "Mediators in the cardiovascular system", p.9, Malta 2-5.6.1994), which were suspended in organ baths and stimulated by vasoconstrictors like phenylephrine. After a stable smooth muscular tonus has been established, the influence on the tonus due to the addition of the abovementioned vasodilators is determined by means of cumulative concentration/effect curves. This is done by adding increasing concentrations of between 1 nM and 10 μM of the vasodilator to the organ bath buffer with no wash-out between the different fractions. In all the aortic rings, addition of the substance caused a stepwise reduction of the contraction in the presence of the vasoconstrictor. The extent of the relaxation is expressed as a percentage of the contraction still remaining at the particular active substance concentration (residual contraction). The 50% effective concentration, $EC_{50}$, represents the potency and is given as the pD2 value (concentration in log M), compared in each case with the known compound PETN, PETriN, PEDN or PEMN of appropriate comparable hydrophilicity or hydrophobicity.

| Compound | pD2 value |
| --- | --- |
| Tri-PA-PETriN ester | −8.4 |
| PETN | −8.3 |
| Me-PETriN ether | −7.9 |
| PETriN | −7.8 |
| Tri-PA methyl ester | −7.8 |
| Bis-PETriN ether | −7.1 |
| Tri-PA amide | −6.8 |
| PEDN | −6.6 |
| Bis-MA diethyl ester | −6.6 |
| Tri-PA | −5.7 |
| PEMN | −5.0 |

Example 44

A typical tablet has the following composition:

| Active substance(s) |  | x mg |
| --- | --- | --- |
| Lactose | DAB 10 | 137 mg |
| Potato starch | DAB 10 | 80 mg |
| Gelatin | DAB 10 | 3 mg |
| Talcum | DAB 10 | 22 mg |
| Magnesium stearate | DAB 10 | 5 mg |
| Silicon dioxide, highly disperse | DAB 10 | 6 mg |
| a) PETriNAc |  | 20 mg |
| b) PETriNAc |  | 80 mg |
| c) PETriNAc |  | 160 mg |
| d) PEDNdAc |  | 20 mg |
| e) PETriN . ⅓H$_2$O |  | 20 mg |
| f) PETriN . ⅓H$_2$O |  | 300 mg |
| g) Tri-PA |  | 20 mg |
| h) Tri-PA |  | 50 mg |
| i) Tri-PA |  | 80 mg |
| j) Tri-PA |  | 160 mg |
| k) Tri-PA |  | 300 mg |
| l) Tri-PA sodium salt |  | 20 mg |
| m) Tri-PA sodium salt |  | 50 mg |
| n) Tri-PA sodium salt |  | 80 mg |
| o) Tri-PA sodium salt |  | 80 mg |
| p) Tri-PA potassium salt |  | 160 mg |
| q) Tri-PA potassium salt |  | 50 mg |
| r) Tri-PA potassium salt |  | 80 mg |

-continued

| Active substance(s) | x mg |
|---|---|
| s) Tri-PA amide | 50 mg |
| t) Tri-PA-NBzl amide | 20 mg |
| u) Tri-PA hydrazide | 20 mg |
| v) Bis-MA diethyl ester | 80 mg |
| w) CN-MA triethyl ester | 80 mg |
| x) Tri-PA-PETriN ester | 20 mg |
| y) Tri-PA-PETriN ester | 50 mg |
| z) Tri-PA-PETriN ester | 80 mg |
| aa) Tri-PA-PETriN ester | 160 mg |
| bb) Tri-BA | 50 mg |
| cc) Tri-BA sodium salt | 50 mg |
| dd) Tri-BA potassium salt | 50 mg |
| ee) Tri-BA methyl ester | 50 mg |
| ff) Me-PETriN ether | 50 mg |
| gg) Bis-PETN ether | 20 mg |
| hh) Bis-PEDN ether | 20 mg |

Example 45

A pump spray contains the following:

| a) Tri-PA | 0.05 wt. % in water |
|---|---|
| b) Tri-PA | 0.3 wt. % in water |
| c) Tri-PA | 5 wt. % in water |
| d) Tri-PA | 10 wt. % in water |
| e) Tri-PA sodium salt | 0.3 wt. % in water |
| f) Tri-PA sodium salt | 5 wt. % in water |
| g) Tri-PA potassium salt | 0.3 wt. % in water |
| h) Tri-PA potassium salt | 5 wt. % in water |
| i) Tri-BA sodium salt | 0.3 wt. % in water |
| j) Tri-BA sodium salt | 5 wt. % in water |
| k) Tri-BA potassium salt | 0.3 wt. % in water |
| l) Tri-BA potassium salt | 5 wt. % in water |

Example 46

The detonation properties of the compounds are determined by the known methods of measuring the expansion capacity, the detonation velocity, the impact pressure and the sensitivity to initiation (Ullmanns Encyklopädie der technischen Chemie (Ullmanns Encyclopaedia of Chemical Technology), vol. 16, 3rd edition, Urban & Schwarzenberg, Munich-Berlin, 1965).

Example 47
[3-Nitryloxy-2,2-bis(nitryloxymethyl)propyl]phosphorylcholine

A solution of 1.35 g of PETriN (5.0 mmol) in 25 ml of chloroform is added dropwise at 0° C. over 30 min, under argon, to a stirred solution of 3.5 ml (26 mmol) of triethylamine and 0.81 g (5.25 mmol) of phosphoryl chloride in 30 ml of chloroform. After the cooling has been removed, the mixture is stirred for 1 h. It is then cooled to 0° C. again and a solution of 2.06 g (7.5 mmol) of choline tosylate in 60 ml of pyridine is rapidly added dropwise, after which the mixture is stirred for 15 h at room temperature. A (saturated) solution of 3.5 g of NaHCO$_3$ in water is added, the mixture is evaporated under vacuum and the residue is taken up in methylene chloride and filtered. The crude product obtained after evaporation of the solvent under vacuum is purified by column chromatography on silica gel (hexane/ethyl acetate/methanol=1:1:1) to give 830 mg of [3-nitryloxy-2,2-bis(nitryloxymethyl)propyl]phosphorylcholine as a colourless oil. Yield: 37%. Elemental analysis: (C: conforms, H: conforms, N: conforms, P: conforms).

What is claimed is:

1. Compounds of general formula I:

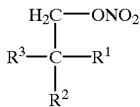

in which
R$^1$, R$^2$, R$^3$ are identical to or different from one another and are CH$_2$—ONO$_2$, CH$_2$—OR$^4$ or R$^5$, at least one of the substituents R$^1$ to R$^2$ being R$^5$,
R$^4$ is H or C$_1$- to C$_6$-alkanoyl,
R$^5$ is COR$^6$,
R$^6$ is OH, OR$^7$, NH$_2$, NHR$^7$, NR$^7_2$, N$^+$R$^7_3$X, NR$^8$, NR$^9$R$^{10}$, NR$^{11}$R$^{12}$ or NH—NH$_2$,
R$^7$ is linear or branched C$_1$- to C$_6$-alkyl, linear or branched C$_1$- to C$_6$-alkenyl, aryl, aralkyl, heteroaryl or heteroaralkyl,
R$^8$ is C$_1$- to C$_6$-alkylidene,
R$^9$, R$^{12}$ are different from one another and are R$^7$
R$^{11}$, R$^{12}$ are identical to or different from one another and are NR$^7_2$, N$^+$R$^7_3$X or NR$^8$, and
X is a halogen or a suitable anion,
and therapeutically acceptable salts thereof, with the exception of the following compounds:
a) 3-nitryloxy-2,2-bis(nitryloxymethyl)propionic acid and
b) methyl 3-nitryloxy-2,2-bis(nitryloxymethyl)propionate.

2. Compounds according to claim 1 of formulae IX to XIII:

 (II)

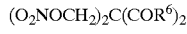 (III)

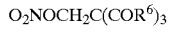 (IV)

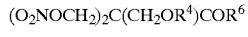 (V)

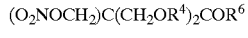 (VI)

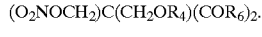 (VII)

3. Compounds according to claim 2 in which
R$^4$ is H or C$_1$- to C$_6$-alkanoyl, and
R$^6$ OH, OR$^7$, NH$_2$, NHR$^7$, NR$^7_2$ or N$^+$R$^7_3$X$^-$.

4. Ethyl 3-nitryloxy-2,2 bis(nitryloxymethyl)propionate, propyl 3-nitryloxy-2,2 bis(nitryloxymethyl)propionate, butyl 3-nitryloxy-2,2-bis(nitryloxymethyl)propionate, benzyl 3-nitryloxy-2,2-bis(nitryloxymethyl)propionate, 3-nitryloxy-2,2-bis(nitryloxymethyl)propionamide, 3-nitryloxy-2,2-bis(nitryloxymethyl)propionic acid N-benzylamide, 3-nitryloxy-2,2-bis(nitryloxymethyl)propionic acid hydrazide, dimethyl 2,2-bis(nitryloxymethyl)malonate, and dimethyl 2-methoxycarbonyl-2-nitryloxymethylmalonate.

5. Compounds according to claim 2 of formulae IX to XIII:

$$(O_2NOCH_2)_2C(COOH)_2 \quad (IX)$$

$$O_2NOCH_2C(COOH)_3 \quad (X)$$

$$(O_2NOCH_2)_2C(CH_2OH)COOH \quad (XI)$$

$$(O_2NOCH_2)C(CH_2OH)_2COOH \quad (XII)$$

$$(O_2NOCH_2)C(CH_2OH)(COOH)_2. \quad (XIII)$$

6. Sodium 3-nitryloxy-2,2-bis(nitryloxymethyl)propinate and potassium 3-nitryloxy-2,2-bis(nitryloxymethyl) propionate.

7. Compounds of general formula I:

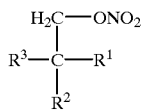

in which
R$^1$, R$^2$, R$^3$ are identical to or different from one another and are CH$_2$—ONO$_2$
CH$_2$—OR$^4$ or R$^5$, at least one of the substituents R$^1$ to R$^3$ being R$^5$,
R$^4$ is H or C$_1$- to C$_6$-alkanoyl,
R$^5$ is COR$^6$,
R$^6$ is Cl or Br for at least one of the substituents or is OH, OR$^7$, NH$_2$, NHR$^7$, NR$^7_2$, N$^+$R$^7_3$X$^-$, NR$^8$, NR$^9$R$^{10}$, NR$^{11}$R$^{12}$ or NH—NH$_2$,
R$^7$ is linear or branched C$_1$- to C$_6$-alkyl, linear or branched C$_1$- to C$_6$-alkenyl, aryl, aralkyl, heteroaryl or heteroaralkyl,
R$^8$ is C$_1$- to C$_6$-alkylidene,
R$^9$, R$^{10}$ are different from one another and are R$^7$,
R$^{11}$, R$^{12}$ are identical to or different from one another and are NR$^7_2$, N$^+$R$^7_3$X$^-$ or NR$^8$, and
X is a halogen or a suitable anion.

8. 3-nitryloxy-2,2-bis(nitryloxymethyl)propionyl chloride,
2,2-bis(nitryloxymethyl)malonyl dichloride, and
2-chlorocarbonyl-2-nitryloxymethymalonyl dichloride.

9. Compounds according to claims 1 or 6 as drugs.

10. Compounds according to claims 1 or 6 as vasodilators.

11. Compounds according to claims 1 or 6 as endothelium-protecting agents.

12. Compounds according to claims 1 or 6 as agents for the treatment of oxidative stress in organisms.

13. Compounds according to claim 12 as agents for the treatment of oxidative stress in mammalian vessels and tissues.

14. Compounds according to claims 1 or 6 as platelet aggregation inhibitors.

15. Compounds according to claims 1 or 6 as agents for the treatment of erectile dysfunctions.

16. A pharmaceutical composition containing one or more of the compounds according to claims 1 or 6.

17. The pharmaceutical composition according to claim 16, further comprising an active substance used for the treatment of cardiovascular diseases.

18. Method for a therapeutic treatment of a human or animal organism using the compounds according to claims 1 or 6.

19. Process for the preparation of 3-nitryloxy-2,2-bis (nitryloxymethyl)propionic acid, wherein 3-nitryloxy-2,2-bis(nitryloxymethyl)propanol is oxidized directly to 3-nitryloxy-2,2-bis(nitryloxymethyl)propionic acid.

20. Process according to claim 19, wherein potassium permanganate is used as the oxidizing agent.

21. Process for the preparation of methyl 3-nitryloxy-2, 2-bis(nitryloxymethyl)propionate, wherein a 3-nitryloxy-2, 2-bis(nitryloxymethyl)propionyl halide is esterified with methanol.

22. Process for the preparation of methyl 3-nitryloxy-2, 2-bis(nitryloxymethyl)propionate, wherein
a) 3-nitryloxy-2,2-bis(nitryloxymethyl)propionic acid is converted to a 3-nitryloxy-2,2-bis(nitryloxymethyl) propionyl halide, and
b) this acid halide is then esterified with methanol.

23. Process according to claim 22, wherein the preparation is carried out without isolation of the 3-nitryloxy-2,2-bis(nitryloxymethyl)propionyl halide.

24. The pharmaceutical composition according to claim 1, wherein the active substance for treatment of a cardiovascular disease is selected from the group consisting of an ACE inhibitor, an antiatherosclerotic, an antihypertensive, a beta-blocker, a cholesterol depressant, a diuretic, a calcium antagonist, a coronary dilator, a lipid depressant, a peripheral vasodilator, and a platelet aggregation inhibitor.

25. A method of treating cardiovascular diseases or protecting vessels and tissues comprising administration of a pharmaceutical composition of claims 16, 17, or 24.

26. Method for a therapeutic treatment of a human or animal organism using a pharmaceutical composition according to claims 16, 17, or 24.

27. The process of claim 22, wherein the 3-nitryloxy-2, 2-bis(nitryloxymethyl)propionyl halide is 3-nitryloxy-2,2-bis(nitryloxymethyl)propionyl chloride.

* * * * *

UNITED STATES PATENT AND TRADEMARK OFFICE
CERTIFICATE OF CORRECTION

PATENT NO. : 6,180,664
DATED : January 30, 2001
INVENTOR(S) : Ulrich Hess, Anne-Katrin Windeck, Holger Brosig.

It is certified that error appears in the above-identified patent and that said Letters Patent is hereby corrected as shown below:

Column 22, Line 13, replace "$R^1$ to $R^2$" with —$R^1$ to $R^3$—;

Column 22, Line 34, replace "formulae IX to XIII" with —formulae II to VII—;

Column 22, Line 49, replace $(O_2NOCH_2)$ C $(CH_2OR_4)$ $(COR_6)_2$ with —$(O_2NOCH_2)$ C $(CH_2OR^4)$ $(COR^6)_2$—; and Column 22, Line 54, replace $R^6$ OH with —$R^6$ is OH—.

Signed and Sealed this

Fifth Day of June, 2001

*Attest:*

*Attesting Officer*

NICHOLAS P. GODICI
*Acting Director of the United States Patent and Trademark Office*